United States Patent [19]

Covey et al.

[11] Patent Number: 4,618,365

[45] Date of Patent: Oct. 21, 1986

[54] SUBSTITUTED TETRAZOLINONES AND THEIR USE AS HERBICIDES

[75] Inventors: Rupert A. Covey, Bethany; Patricia J. Forbes, Waterbury; Allyn R. Bell, Cheshire, all of Conn.

[73] Assignee: Uniroyal Chemical Company, Inc., Middlebury, Conn.

[21] Appl. No.: 560,031

[22] Filed: Dec. 9, 1983

[51] Int. Cl.⁴ ............... C07D 401/06; C07D 257/04; A01N 43/67

[52] U.S. Cl. ........................... 71/92; 546/210; 548/251; 71/88

[58] Field of Search ............ 548/251; 546/210; 424/269; 71/92

[56] References Cited

PUBLICATIONS

R. Elderfield (ed.) "Heterocyclic Compounds", vol. 8, Wiley, N.Y., N.Y. (1967) pp. 78–85.
Tsuge et al., J. Org. Chem., 45, p. 5130 (1980).
Vandensavel, J. Org. Chem. 38, p. 675 (1973).

Primary Examiner—Glennon H. Hollrah
Assistant Examiner—D. B. Springer
Attorney, Agent, or Firm—William E. Dickheiser

[57] ABSTRACT

A compound having the formula the formula

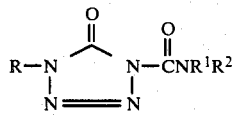

where R is $C_1-C_{12}$ alkyl, $C_5-C_6$ cycloalkyl, $C_2-C_{13}$ alkoxyalkyl, $C_7-C_9$ aralkyl, phenyl, naphthyl, phenyl substituted with F, Cl, Br, I, $C_1-C_4$ alkyl, $C_1-C_4$ alkoxy, methylenedioxy, $NR^3R^4$ wherein $R^3$ and $R^4$ are the same or different and are hydrogen or $C_1-C_6$ alkyl, $C_2-C_5$ alkoxycarbonyl, phenoxy, $NO_2$, cyano, trihalomethyl or trihalomethoxy where halo is F, Cl or Br or benzyl substituted with F, Cl, Br, I, $C_1-C_4$ alkyl, $C_1-C_4$ alkoxy, methylenedioxy, $C_2-C_5$ alkoxycarbonyl, carboxy, phenoxy, $NO_2$, cyano, trihalomethyl or trihalomethoxy where halo is F, Cl or Br; $R^1$ and $R^2$ are the same or different and are $C_1-C_6$ alkyl, $C_3-C_6$ alkenyl, $C_5-C_6$ cycloalkyl or $R^1$ and $R^2$ together are $C_4-C_8$ alkylene or $C_4-C_8$ oxydialkylene is disclosed.

Furthermore, a process for forming this compound by reacting a compound having the formula

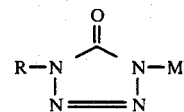

wherein M is hydrogen or an alkali metal such as Li, Na or K and R has the meanings given above with a carbamoyl halide having the formula $XCONR^1R^2$, wherein X is chlorine or bromine and $R^1$ and $R^2$ have the meanings above is taught.

In addition, a method of controlling weeds, both pre-emergence and postemergence, using a herbicidally effective amount of the compound of this invention is set forth.

Finally, a composition is disclosed, comprising the compound of this invention and a carrier therefor.

7 Claims, No Drawings

SUBSTITUTED TETRAZOLINONES AND THEIR USE AS HERBICIDES

BACKGROUND OF THE DISCLOSURE

1. Field of the Invention

The instant invention is directed to a new class of substituted tetrazolinone compounds. More specifically, the instant invention relates to a new class of substituted tetrazolinone compounds which are useful as pre-emergence and post-emergence herbicides.

2. Background of the Prior Art

The synthesis of substituted tetrazolinones is known in the art. Horwitz, et al, JACS, 81 3076 (1959) and Tsuge et al, J. Org. Chem, 45 5130 (1980) provide methods for synthesizing tetrazolinones. These disclosures provide no utility for the classes of substituted tetrazolinones synthesized.

The need for effective herbicides, both pre-emergence and post-emergence needs no special emphasis. The control of weeds and undesirable vegetation is of great economic importance since weed competition inhibits the production of foliage, fruit or seed of agricultural crops. The presence of weeds can reduce harvesting efficiency and the quality of the harvested crop. Weed control is essential for maximum production of many agronomic and horticultural crops including corn, (Zea mays L.), cotton (Gossypium SP), sunflower (Helianthus annus L.) and soybeans (Glycine max (L.) Merr.) Weeds on noncropped areas may cause a fire hazard, undesirable drifting of sand or snow, or irritation to persons with allergies. Thus, suppression of undesirable weed growth is very advantageous.

SUMMARY OF THE INVENTION

It has now been found that a new class of substituted tetrazolinones unexpectedly provides excellent pre-emergence and post-emergence herbicidal properties.

In accordance with the instant invention a compound having the formula

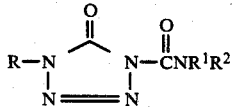

where R is $C_1$–$C_{12}$ alkyl, $C_2$–$C_{13}$ alkoxyalkyl, $C_7$–$C_9$ aralkyl, $C_5$–$C_6$ cycloalkyl, phenyl, naphthyl, phenyl substituted with F, Cl, Br, I, $C_1$–$C_4$ alkyl, $C_1$–$C_4$ alkoxy, methylenedioxy, $NR^3R^4$ wherein $R^3$ and $R^4$ are the same or different and are hydrogen or $C_1$–$C_6$ alkyl, $C_2$–$C_5$ alkoxycarbonyl, carboxy, phenoxy, $NO_2$, cyano, trihalomethyl or trihalomethoxy wherein halo is F, Cl or Br or benzyl substituted with F, Cl, Br, I, $C_1$–$C_4$ alkyl, $C_1$–$C_4$ alkoxy, methylenedioxy, $C_2$–$C_5$ alkoxycarbonyl, phenoxy, $NO_2$, cyano, trihalomethyl or trihalomethoxy wherein halo is F, Cl or Br; $R^1$ and $R^2$ are the same or different and are $C_1$–$C_6$ alkyl, $C_3$–$C_6$ alkenyl, $C_5$–$C_6$ cycloalkyl or $R^1$ and $R^2$ together are $C_4$–$C_8$ alkylene or $C_4$–$C_8$ oxydialkylene is disclosed.

In further accordance with the instant invention a composition is provided comprising the compound of this invention with a carrier.

In still further accordance with the present invention a method for controlling weeds and undesirable vegetation employing the composition of this invention is taught.

DETAILED DESCRIPTION

The present invention is directed to a compound having the structural formula

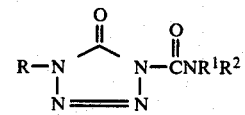

where R is $C_1$–$C_{12}$ alkyl, $C_2$–$C_{13}$ alkoxyalkyl, $C_7$–$C_9$ aralkyl, phenyl, naphthyl, phenyl substituted with F, Cl, Br, I, $C_1$–$C_4$ alkyl, $C_1$–$C_4$ alkoxy, methylenedioxy, $NR^3R^4$ wherein $R^3$ and $R^4$ may be the same or different and are hydrogen or $C_1$–$C_6$ alkyl, $C_2$–$C_5$ alkoxycarbonyl, carboxy, phenoxy, $NO_2$, cyano, trihalomethyl or trihalomethoxy where halo is F, Cl or Br or benzyl substituted with F, Cl, Br, I, $C_1$–$C_4$ alkyl, $C_1$–$C_4$ alkoxy, methylenedioxy, $C_2$–$C_5$ alkoxycarbonyl, phenoxy, $NO_2$, cyano, trihalomethyl or trihalomethoxy where halo is F, Cl or Br; $R^1$ and $R^2$ are the same or different and are $C_1$–$C_6$ alkyl, $C_3$–$C_6$ alkenyl, $C_5$–$C_6$ cycloalkyl or $R^1$ and $R^2$ together are $C_4$–$C_8$ alkylene or $C_4$–$C_8$ oxydialkylene.

More preferable, the invention is directed to a compound having the structural formula given above where R is phenyl or phenyl substituted with F, Cl, Br, I, methyl, methoxy, ethoxy, ethoxycarbonyl or phenoxy; and $R^1$ and $R^2$ are the same and are $C_1$–$C_3$ alkyl or together are tetramethylene.

The compounds of this invention are prepared by either reacting a tetrazolinone compound having the formula

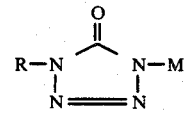

wherein M is hydrogen or alkali metal such as Li, Na or K with a carbamoyl halide having the formula $XCONR^1R^2$, wherein X is chlorine or bromine and $R^1$ and $R^2$ have the meanings above. When M is hydrogen, the reaction is preferably conducted in the presence of a suitable acid acceptor such as pyridine, tertiary amine, e.g. triethylamine. It is noted that this tetrazolinone compound may be synthesized by the methods disclosed in the Horwitz et al and Tsuge et al references mentioned above. The equivalent ratio of X/M (as representative of the above reactants) may vary from 0.75/1 to 2/1, preferably from 0.9/1 to 1.5/1. Excess of M may be advantageous in the purification of product since the M-type tetrazolinone is soluble in base. The reaction temperature may range from 40° C. to the boiling point of the solvent used, usually the reaction is conducted under reflux conditions. Suitable solvents are those which are inert to the reactant, such as acetone, acetonitrile, toluene, chloroform and the like. The reaction time ranges from 0.1 to 48 hours or longer. Usually, the reaction is complete in 1 to 24 hours.

The instant invention is also directed to a composition comprising the substituted tetrazolinone compound of this invention and a carrier therefor. The carrier employed in a preferred embodiment of this invention is a finely-divided or granular inorganic or organic material such as attapulgite clay, sand, vermiculite, ground corn cobs, activated carbon and the like. The compound of this invention may be impregnated on the finely-divided or granular material.

The carrier may also be an inert powder. Preferably, the inert powder is one of the mineral silicates, e.g., mica, talc, pyrophyllite and clays. In this case, the composition is formed by grinding the compound of this invention into a fine powder and mixing it with the inert powder to which a surface active dispersing agent has been added.

A third carrier is the combination of the above inert powder and water. This carrier employs the wettable powder dispersed in water.

Yet another carrier is a solvent and water. In this embodiment the compound of this invention is dissolved in a solvent such as benzene, toluene or other aliphatic or aromatic hydrocarbon. An emulsifiable concentrate is formed with the addition of a surface active and/or dispersing agent. The emulsifiable concentrate is then dispersed in water. In this composition water solubility may be increased using a cosolvent system involving acetone, dimethyl sulfoxide or other water miscible solvent.

It is noted that the surface active agents preferred for use in the composition of this invention are well known to those skilled in the art. In addition, suitable surface active agents for use in the composition of this invention are provided in McCutcheon's Detergents and Emulsifiers, 1970, Allured Publishing Corp., Ridgewood, N.J.; U.S. Pat. No. 2,614,916, columns 2 to 4; and U.S. Pat. No. 2,547,727, columns 3 and 4.

The present invention is furthermore directed to a method of controlling weeds, both pre-emergence and post-emergence, by application of a herbicidally effective amount of the composition of this invention.

In the case where the composition comprises impregnated granules of the compound of this invention, application, to control weeds, is by spreading on the soil. The wettable powder may be similarly applied. In the case where the wettable powder is dispersed in water, this composition controls weeds by spraying the dispersion on weeds or unwanted vegetation or onto the soil surface. Where an emulsion is formed that emulsion is likewise sprayed onto the weeds or onto the soil surface.

The concentration of the compound of this invention in the composition of this invention may vary widely, e.g. from 1 to 95%. The concentration of active compound in dispersions applied to the soil or foliage is almost invariably from 0.002% to 75%.

For use as preemergence herbicides the compound of this invention is frequently applied at rates of 0.05 to 25 pounds per acre (0.056 to 28 kg/ha) to soil which contains weed and crop seed, namely either to the surface of the soil or incorporated into the upper one to three inches (2.5 to 7.5 cm.) of soil. As postemergence herbicides, the chemicals are typically applied at rates of 0.05 to 25 pounds per acre (0.056 to 28 kg/ha) to the foliage of weeds. The chemicals may be employed singly or as a mixture of two or more chemicals.

The most suitable rate of application in any given case may depend on such factors as soil type, soil pH, soil organic matter content, the quantity and intensity of rainfall before and after treatment the air and soil temperature, light intensity and light duration per day. All of these factors can have an influence on the efficacy of the chemicals for a given weed control use.

The herbicidal use may include control of vegetation at industrial sites or selective weed control in crop fields.

The following examples are given to illustrate the invention. Since these examples are illustrative of the invention, the invention should not be deemed to be limited thereto.

EXAMPLE 1

Preparation of 1-(2-ethoxyphenyl)-5(4H)-tetrazolinone

Aluminum chloride (15.0 g, 0.11 mol) was added in small portions while stirring to 75 ml of tetrahydrofuran (THF, tested for absence of peroxide), keeping the temperature of the solution below 30° C. 2-Ethoxyphenyl isocyanate (16.2 g, 0.1 mole), 50 ml THF and 19.5 g, (0.3 mol) of sodium azide were combined in a separate flask, equipped with a condenser and thermometer. The aluminum chloride solution was added to the flask and the mixture was refluxed at 70° to 80° C. for 16 hours. The mixture was cooled to room temperature, and 10 ml of concentrated hydrochloric acid and 10 ml of water were added in one portion to the stirred mixture. The mixture was warmed slightly, and nitrogen was swept over the surface to remove unreacted hydrazoic acid. The mixture was stirred for 20 minutes and filtered. The salt was washed twice with 50 ml portions of THF. The THF layers were combined and after concentration under reduced pressure the product crystallized. After recrystallization from ethanol, 10.0 g (50%) of white crystals were obtained, mp 115°–116° C. The structure was confirmed by infrared (IR) and nuclear magnetic resonance (NMR) analyses.

This compound was subsequently reacted with N,N-dimethylcarbamyl chloride resulting in Compound No. 20 of Table I.

EXAMPLE 2

Preparation of 1-(2,5-dimethoxyphenyl)-4-(N,N-dimethylcarbamyl)-5(4H)-tetrazoline (Cpd. No. 19)

Potassium carbonate (6.6 g 0.048 mol), 50 ml of acetonitrile and 4.4 g (0.02 mol) of 1-(2,5-di-methoxyphenyl)-5(4H)-tetrazolinone were combined and refluxed at 85° C. for 15 minutes. The mixture was cooled to room temperature, and 3.2 g (0.3 mol) of dimethylcarbamyl chloride was added in one portion. The mixture was refluxed at 80°–85° C. for one hour, cooled and the salt removed by filtration. After the removal of the solvent under reduced pressure, the product crystallized. The product was recrystallized from ethanol, giving 4.0 g (69% yield) of white crystals, m.p. 125°–6° C.

The structure was confirmed by IR and NMR spectra.

EXAMPLE 3

Preparation of 1-phenyl-4-(N,N-diethylcarbamyl)-5(4H)-tetrazolinone (Cpd. No. 2)

1-Phenyl-5(4H)-tetrazolinone (4.8 g, 0.03 mol), 5.4 g (0.04 mol) of potassium carbonate and 50 ml of acetonitrile were combined and refluxed at 80° C. for 10 minutes. The mixture was cooled to room temperature, and 5.4 g (0.04 mol) of diethylcarbamyl chloride was added in one portion. The reaction mixture was refluxed at 80°–90° C. for 16 hours, cooled, and salt removed by filtration. The filtrate was poured into 75 ml of H$_2$O, and a white precipitate was formed. The product was recrystallized from 25 ml of ethanol and 5 ml of hexane, giving 4.5 g (57% yield) of white crystals, m.p. 66°-8° C. The structure was confirmed by IR and NMR-spectra.

As essentially described above, a series of chemicals of this invention was prepared as summarized in Table I.

TABLE I

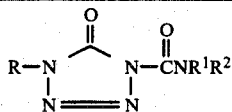

| Cpd. No. | R | R¹ | R² | m.p. °C. |
|---|---|---|---|---|
| 1 | $C_6H_5$ | $CH_3$ | $CH_3$ | 114–115 |
| 2 | " | $C_2H_5$ | $C_2H_5$ | 66–68 |
| 3 | " | $i\text{-}C_3H_7$ | $i\text{-}C_3H_7$ | 67–68 |
| 4 | " | —$CH_2CH_2CH_2CH_2$— | | 94–96 |
| 5 | " | $C_6H_5$ | $C_6H_5$ | 140–141 |
| 6 | 2-F—$C_6H_4$ | $CH_3$ | $CH_3$ | 161–163 |
| 7 | 2-Cl—$C_6H_4$ | " | " | 126–128 |
| 8 | 3-Cl—$C_6H_4$ | " | " | 110–112 |
| 9 | 4-Cl—$C_6H_4$ | " | " | 144–145 |
| 10 | 2,4,5-$Cl_3$—$C_6H_2$ | " | " | 145–147 |
| 11 | 4-$CH_3$—$C_6H_4$ | " | " | 127–128 |
| 12 | 4-$CH_3$—$C_6H_4$ | $C_2H_5$ | $C_2H_5$ | 65–67 |
| 13 | 3,4-$(CH_3)_2$—$C_6H_3$ | $CH_3$ | $CH_3$ | 99–101 |
| 14 | 2,4,6-$(CH_3)_3$—$C_6H_2$ | " | " | 94–96 |
| 15 | 3-$CF_3$—$C_6H_4$ | " | " | 80–82 |
| 16 | 4-$CH_3O$—$C_6H_4$ | " | " | 145–147 |
| 17 | 2,4-$(CH_3O)_2$—$C_6H_3$ | " | " | 126 |
| 18 | 3,4,5-$(CH_3O)_3$—$C_6H_2$ | " | " | 136–138 |
| 19 | 2,5-$(CH_3O)_2$—$C_6H_3$ | " | " | 125–126 |
| 20 | 2-$C_2H_5O$—$C_6H_4$ | $C_2H_5$ | $C_2H_5$ | oil |
| 21 | 2-$C_2H_5O$—$C_6H_4$ | $CH_3$ | $CH_3$ | 87–89 |
| 22 | $C_2H_5OOC$—$C_6H_4$ | " | " | 76–78 |
| 23 | 4-$C_6H_5O$—$C_6H_4$ | " | " | 110–112 |
| 24 | 3,4-$Cl_2$—$C_6H_4$ | " | " | 147–149 |

Following essentially the procedures outlined above additional compounds within the scope of this invention are prepared. These compounds, compounds 25–46, are defined in Table II.

TABLE II

| Cpd. No. | R | R¹ | R² |
|---|---|---|---|
| 25 | $CH_3$ | $CH_3$ | $CH_3$ |
| 26 | $n\text{-}C_6H_{13}$ | $C_4H_9$ | $C_6H_{13}$ |
| 27 | $C_6H_5$—$C(CH_3)_2$ | $C_2H_5$ | $C_2H_5$ |
| 28 | 4-$CH_3$—$C_6H_4$—$CH_2$ | $C_2H_5$ | $C_2H_5$ |
| 29 | 2-F—$C_6H_4$—$CH_2$ | $C_6H_{11}$ | $C_2H_5$ |
| 30 | 4-Cl—$C_6H_4$—$CH_2$ | $CH_2CH$=$CH_2$ | $CH_2CH$=$CH_2$ |
| 31 | $CH_3OCH_2$ | $CH_3$ | $CH_3$ |
| 32 | $C_{12}H_{25}OCH_2$ | $C_2H_5$ | $C_2H_5$ |
| 33 | 2-Br—$C_6H_4$—$CH_2$ | $C_{12}H_{25}$ | $CH_3$ |
| 34 | 4-$C_4H_9$—$C_6H_4$—$CH_2$ | $C_2H_5$ | $C_2H_5$ |
| 35 | 3-$CH_3O$—$C_6H_4$—$CH_2$ | $CH_3$ | $CH_3$ |
| 36 | 4-$C_6H_5O$—$C_6H_4$—$CH_2$ | $C_2H_5$ | $C_2H_5$ |
| 37 | 3,4-$(CH_2O_2)C_6H_3CH_2$ | $CH_3$ | $CH_3$ |
| 38 | 2,3-$(CH_2O_2)C_6H_3$ | $CH_3$ | $CH_3$ |
| 40 | $(Cl_3CO)C_6H_4$ | $i\text{-}C_3H_7$ | $i\text{-}C_3H_7$ |
| 41 | 3-$CF_3$—$C_6H_4$—$CH_2$ | $CH_3$ | $CH_3$ |
| 42 | 3-$NO_2$—$C_6H_4$ | $CH_3$ | $CH_3$ |
| 43 | 3-CN—$C_6H_4$ | —$(CH_2)_6$— | |
| 44 | 2-$(CH_3)_2N$—$C_6H_4$ | $C_5H_9$ | $CH_3$ |
| 45 | 2-(COOH)—$C_6H_4$ | $C_2H_5$ | $C_2H_5$ |
| 46 | $C_6H_{11}$ | $C_3H_7$ | $C_3H_7$ |

EXAMPLE 4

To illustrate the effectiveness of the previously described substituted tetrazolinones of this invention as preemergence herbicides, 300 mg chemical was dissolved in 10 ml acetone to which 30 mg emulsifying agent, ethoxylated sorbitan monolaurate, was added. The solution was diluted to 100 ml with distilled water. Ten milliliters of this 3000 ppm solution was diluted to 250 ppm with distilled water. The chemical was applied at the rate of 10 lb/A (11.2 kg/ha) by drenching 46 ml of the 250 ppm solution on the surface of soil in 4½ inch (11.25 cm) plastic pots wherein seeds of the following weeds had been planted: velvetleaf (*Abutilon theophrasti medic*) (VL), jimsonweed (*Datura stramonium* L.) (JW), tall morninglory (*Ipomea purpurea* L. Roth) (TM), switchgrass (*Panicum virgatum* L.) (SG), barnyardgrass (*Echinochloa crusgalli* (L.) Beauv.) (BG), green foxtail (*Setaria viridis* (L.), Beauv.) (GF). The percent control of the weeds compared to untreated checks was determined two weeks after treatment. TABLE III summarizes the results achieved with compounds formulated as indicated above, and the data clearly indicate the good to excellent herbicidal efficacy of compounds of this invention.

TABLE III

| | Preemergence Activity (% Control at 11.2 kg/ha) | | | | | |
|---|---|---|---|---|---|---|
| Cpd. No. | VL | JW | TM | BG | SG | GF |
| 1 | 0 | 0 | 0 | 100 | 100 | 100 |
| 2 | 0 | 0 | 0 | 100 | 100 | 100 |
| 3 | 0 | 0 | 0 | 100 | 100 | 100 |
| 4 | 0 | 0 | 0 | 100 | 100 | 100 |
| 5* | — | — | — | 50 | 50 | 0 |
| 6 | 50 | 30 | 50 | 100 | 100 | 100 |
| 7 | 0 | 0 | 0 | 100 | 100 | 100 |
| 8 | 90 | 0 | 0 | 100 | 95 | 95 |
| 9 | 0 | 0 | 0 | 75 | 100 | 80 |
| 10 | 0 | 0 | 0 | 75 | 95 | 100 |
| 11 | 0 | 0 | 0 | 98 | 100 | 100 |
| 12 | 0 | 0 | 0 | 100 | 100 | 100 |
| 13 | 0 | 0 | 0 | 100 | 100 | 100 |
| 14 | 0 | 0 | 0 | 100 | 100 | 100 |
| 15 | 0 | 0 | 0 | 100 | 100 | 100 |
| 16 | 0 | 0 | 0 | 100 | 100 | 100 |
| 17 | 0 | 0 | 0 | 100 | 100 | 100 |
| 18 | 0 | 0 | 0 | 100 | 100 | 100 |
| 19 | 50 | 0 | 25 | 100 | 100 | 100 |
| 20 | — | — | — | 100 | 100 | 100 |
| 21 | 25 | 0 | 0 | 100 | 100 | 100 |
| 22 | 50 | 75 | 0 | 100 | 100 | 100 |
| 23 | 100 | 0 | 0 | 90 | 95 | 25 |
| 24* | 0 | 0 | 0 | 40 | 50 | 20 |

*at 22.4 kg/ha

EXAMPLE 5

To illustrate effectiveness of the described substituted tetrazolinones as postemergence herbicides, the 3000 ppm solution described under Example 4 was atomized with a conventional DeVilbiss [trademark] sprayer, wetting the foliage to the drip point. The weeds, which were the same species as described under Example 4 were treated six days after emergence. The percent weed control was evaluated two weeks after treatment. Table IV illustrates the postemergence herbicidal efficacy of chemicals of this invention.

TABLE IV

| | Postemergence Activity (% Control at 3000 ppm) | | | | | |
|---|---|---|---|---|---|---|
| Cpd. No. | VL | JW | TM | BG | SG | GF |
| 1* | 0 | 0 | 35 | 85 | 95 | 90 |
| 2 | 0 | 0 | 5 | 100 | 75 | 100 |
| 3 | 10 | 0 | 25 | 5 | 0 | 15 |
| 4 | 0 | 5 | 5 | 80 | 25 | 45 |
| 5* | 90 | 100 | 10 | 0 | 90 | 95 |

TABLE IV-continued

| | Postemergence Activity (% Control at 3000 ppm) | | | | | |
|---|---|---|---|---|---|---|
| Cpd. No. | VL | JW | TM | BG | SG | GF |
| 6 | 0 | 0 | 5 | 55 | 5 | 25 |
| 7 | 15 | 10 | 5 | 35 | 15 | 15 |
| 8 | 0 | 15 | 30 | 90 | 10 | 100 |
| 9 | 0 | 0 | 10 | 75 | 90 | 75 |
| 10 | 0 | 0 | 10 | 60 | — | 75 |
| 11 | 0 | 5 | 25 | 85 | 95 | 90 |
| 12 | 0 | 0 | 35 | 85 | 20 | 50 |
| 13 | 0 | 0 | 25 | 80 | 85 | 75 |
| 14 | 75 | 0 | 40 | 50 | 85 | 20 |
| 15 | 50 | 95 | 100 | 100 | 100 | 100 |
| 16 | 0 | 0 | 50 | 40 | 60 | 55 |
| 17 | 15 | 0 | 10 | 0 | 0 | 0 |
| 18 | 0 | 5 | 5 | 20 | 0 | 10 |
| 19 | 0 | 0 | 5 | 10 | 15 | 5 |
| 20 | — | 70 | 85 | 95 | — | 90 |
| 21 | 5 | 65 | 45 | 25 | 75 | 15 |
| 22 | 5 | 0 | 35 | 50 | 10 | 15 |
| 23 | 25 | 50 | 90 | 85 | — | 65 |
| 24 | 0 | 0 | 0 | 40 | 50 | 15 |

*at 6000 ppm

Similar pre- and postemergence herbicidal results are achieved with Cpd. Nos. 25–46 when applied to weeds in a manner indicated in Examples 4 and 5.

The above embodiments and examples illustrate the scope and spirit of the instant invention. These embodiments and examples will make apparent, to those skilled in the art, other embodiments and examples within the scope of the present invention. Therefore, the instant invention should be limited only by the appended claims.

What is claimed is:

1. A compound having the formula

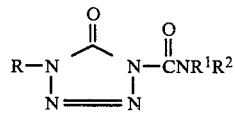

where R is $C_1-C_{12}$ alkyl, $C_5-C_6$ cycloalkyl, $C_2-C_{13}$ alkoxyalkyl, $C_7-C_9$ aralkyl, phenyl, naphthyl, phenyl substituted with F, Cl, Br, I, $C_1-C_4$ alkyl, $C_1-C_4$ alkoxy, methylenedioxy, $NR^3R^4$ wherein $R^3$ and $R^4$ are the same or different and are hydrogen or $C_1-C_6$ alkyl, $C_2-C_5$ alkoxycarbonyl, carboxy, phenoxy, $NO_2$, cyano, trihalomethyl or trihalomethoxy wherein halo is F, Cl or Br or benzyl substituted with F, Cl, Br, I, $C_1-C_4$ alkyl, $C_1-C_4$ alkoxy, methylenedioxy, $C_2-C_5$ alkoxycarbonyl, phenoxy, $NO_2$, cyano, trihalomethyl or trihalomethoxy wherein halo is F, Cl or Br; $R^1$ and $R^2$ are the same or different and are $C_1-C_6$ alkyl, $C_3-C_6$ alkenyl, $C_5-C_6$ cycloalkyl or $R^1$ and $R^2$ together are $C_4-C_8$ alkylene.

2. A compound in accordance with claim 1 where R is phenyl or phenyl substituted with F, Cl, Br, I, methyl, methoxy, ethoxy, ethoxycarbonyl or phenoxy; and $R^1$ and $R^2$ are the same and are $C_1-C_3$ alkyl or together are tetramethylene.

3. An herbicidal composition comprising (a) an herbicidally effective amount of a compound having the formula

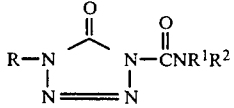

where R is $C_1-C_{12}$ alkyl, $C_5-C_6$ cycloalkyl, $C_2-C_{13}$ alkoxyalkyl, $C_7-C_9$ aralkyl, phenyl, naphthyl, phenyl substituted with F, Cl, Br, I, $C_1-C_4$ alkyl, $C_1-C_4$ alkoxy, methylenedioxy, $NR^3R^4$ wherein $R^3$ and $R^4$ are the same or different and are hydrogen or $C_1-C_6$ alkyl, $C_2-C_5$ alkoxycarbonyl, carboxy, phenoxy, $NO_2$, cyano, trihalomethyl or trihalomethoxy where halo is F, Cl or Br or benzyl substituted with F, Cl, Br, I, $C_1-C_4$ alkyl, $C_1-C_4$ alkoxy, methylenedioxy, $C_2-C_5$ alkoxycarbonyl, phenoxy, $NO_2$, cyano, trihalomethyl or trihalomethyoxy where halo is F, Cl or Br; $R^1$ and $R^2$ are the same or different and are $C_1-C_6$ alkyl, $C_3-C_6$ alkenyl, $C_5-C_6$ cycloalkyl or $R^1$ and $R^2$ together are $C_4-C_8$ alkylene and (b) a suitable carrier.

4. A composition in accordance with claim 3 wherein R is phenyl or phenyl substituted with F, Cl, Br, I, methyl, methoxy, ethoxy, ethoxycarbonyl or phenoxy; and $R^1$ and $R^2$ are the same and are $C_1-C_3$ alkyl or together are tetramethylene.

5. A method for controlling weeds by applying a herbicidally effective amount of a compound having the formula

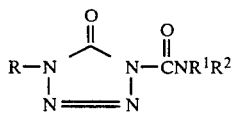

where R is $C_1-C_{12}$ alkyl, $C_5-C_6$ cycloalkyl, $C_2-C_{13}$ alkoxyalkyl, $C_7-C_9$ aralkyl, phenyl, naphthyl, phenyl substituted with F, Cl, Br, I, $C_1-C_4$ alkyl, $C_1-C_4$ alkoxy, methylenedioxy, $NR^3R^4$ wherein $R^3$ and $R^4$ are the same or different and are hydrogen or $C_1-C_6$ alkyl, $C_2-C_5$ alkoxycarbonyl, phenoxy, $NO_2$, cyano, trihalomethyl or trihalomethoxy where halo is F, Cl or Br or benzyl substituted with F, Cl, Br, I, $C_1-C_4$ alkyl, $C_1-C_4$ alkoxy, methylenedioxy, $C_2-C_5$ alkoxycarbonyl, carboxy, phenoxy, $NO_2$, cyano, trihalomethyl or trihalomethoxy where halo is F, Cl or Br; $R^1$ and $R^2$ are the same or different and are $C_1-C_6$ alkyl, $C_3-C_6$ alkenyl, $C_5-C_6$ cycloalkyl or $R^1$ and $R^2$ together are $C_4-C_8$ alkylene.

6. A method in accordance with claim 5 wherein said weeds are controlled by applying said compound to the soil prior to the emergence of said weeds.

7. A method in accordance with claim 5 wherein said weeds are controlled by applying said compound foliarly to said weeds.

* * * * *